US009120844B2

(12) United States Patent
Lee et al.

(10) Patent No.: US 9,120,844 B2
(45) Date of Patent: Sep. 1, 2015

(54) METHOD FOR CHANGING CONFORMATION OF GLOBULAR PROTEINS

(75) Inventors: Yuh-lang Lee, Tainan (TW); Ke-hsuan Wang, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 334 days.

(21) Appl. No.: 13/479,294

(22) Filed: May 24, 2012

(65) Prior Publication Data

US 2013/0095551 A1   Apr. 18, 2013

(30) Foreign Application Priority Data

Oct. 12, 2011 (TW) .............. 100136951 A

(51) Int. Cl.
*C12N 11/00* (2006.01)
*C07K 1/113* (2006.01)
*C12N 9/04* (2006.01)

(52) U.S. Cl.
CPC .............. *C07K 1/113* (2013.01); *C12N 9/0006* (2013.01); *C12N 11/00* (2013.01); *C12Y 101/03004* (2013.01)

(58) Field of Classification Search
CPC ................ C12N 11/00; C12N 9/0006; C12Y 101/03004; C07K 1/113
USPC ............................................. 435/190, 4, 25
See application file for complete search history.

(56) References Cited

PUBLICATIONS

Kudryashova et al., Eur. Biophys. J. 32:553-562, 2003.*
Talham, D.,Chem. Rev. 104:5479-5501, 2004.*
Dai et al., Colloids and Surfaces B: Biointerfaces 13:105-111, 1999.*
Lee et al., Langmuir 23:2042-2051, 2007.*
Ping-Chieh Wu ,A Study o the Adsorption Mechanism of Some Globular Proteins at the Air/ Liquid Interface; Published by :Institute of Biomedical Engineering, National Yang-Ming University Taiwan. Jul. 1999, p. 49-50.
Claudia Schladitz et alAmyloid—B-Sheet Formation at the Air-Water Interface, in Biophysical Journal, vol. 77, Dec. 1999, p. 3305-3310.
Ananthakrishnan Sethuraman et alProtein Structural Perturbation and Aggregation on Homogeneous Surfaces; in Biophysical Journal, vol. 88, Feb. 2005, p. 1322-1333.
Norrde William et al; Surface-Induced Changes in the Structure and Activity of Enzymes Physically Immobilized at Solid/Liquid Interfaces;Biotewchnology applied Biochem ( 1998)28, 133-143.
Wang et al., "Headgroup Effects of Template Monolayers on the Adsorption Behavior and Confirmation of Glucose Oxidase Adsorbed at Air/Liquid Interfaces", Langmuir 2011, 27, 7595-7602, May 24, 2011.

* cited by examiner

*Primary Examiner* — Delia Ramirez
(74) *Attorney, Agent, or Firm* — Mark M Friedman

(57) ABSTRACT

A method for changing conformation of globular proteins is provided. The method controls the concentration of the globular proteins and the adsorption time of the globular proteins from the aqueous solution to the air/liquid interface, so that the main conformation of the globular proteins in a protein monolayer can be changed into β-sheet or α-helix. Meanwhile, the protein monolayer having the conformation of β-sheet or α-helix can be vertically deposited and transferred onto a substrate for various applications according to needs. The present invention can change three-dimensional structures of biological molecules and remain original functions thereof without additionally using any physical/chemical treatment to change the conformation of the globular proteins.

9 Claims, 3 Drawing Sheets

METHOD FOR CHANGING CONFORMATION OF GLOBULAR PROTEINS

CROSS REFERENCE TO RELATED APPLICATIONS

This application claims the priority of Taiwan Patent Application No. 100136951, filed on Oct. 12, 2011. This invention is partly disclosed in a published article by Ke-Hsuan Wang, Mei-Jywan Syu, Chien-Hsiang Chang, and Yuh-Lang Lee, "Headgroup Effects of Template Monolayers on the Adsorption Behavior and Conformation of Glucose Oxidase Adsorbed at Air/Liquid Interfaces" published in *Langmuir* 2011, vol. 27, p. 7595-7602.

FIELD OF THE INVENTION

The present invention relates to a method for changing conformation of globular proteins, and more particularly to a method for changing conformation of a protein monolayer of globular proteins by controlling a concentration of the globular proteins and an adsorption time of the globular proteins from an aqueous solution to an air/liquid interface.

BACKGROUND OF THE INVENTION

Nowadays, the study of biomolecules has become a popular research topic, and people pay more and more attention to the development and manufacture of biomolecular devices. Among various biomolecules, proteins are the main components of living organisms and also the basic substance that life activities rely on. Therefore, it is important to study three dimensional structures of protein molecules and their functions, in order to develop bioengineering. Protein molecules consist of polypeptides of amino acids which are linked together by covalent and non-covalent bonds to form three-dimensional structures with the lowest energy, stable molecular structures and specific physiological functions.

When the environment changed, protein molecules generally adjust their three dimensional structures to maintain energy balances and theirs physiological functions. In an irreversible case, protein molecules, which are subjected to physical or chemical treatment, will loss the regulation of three dimensional structures and theirs physiological functions, wherein this phenomenon is called "protein denaturation". Therefore, if fundamental physiologic functions of protein molecules can be kept and a plurality of three dimensional structures of protein molecules can be obtained, it will be helpful to execute various experiments or applications for physiologic functions of protein molecules. For examples, detection biochips are always constructed by immobilizing specific three dimensional structures (such as α-helix or β-sheet) of proteins onto a detection area thereon, in order to provide effective detecting functions. Therefore, it is necessary to obtain proteins with desired three dimensional structures for a large scale of production application.

The conventional techniques of changing protein conformation generally change protein conformation by physical/chemical treatments, such as acidic solution, basic solution, urea solution, organic solvent, heavy metal, heat, pressure, ultraviolet light, ultrasound and/or X-ray etc. However, in the processes of these physical/chemical treatments, if the conditions of these treatments are not suitably controlled, protein molecules will be irreversibly denatured, and thus loss the regulations of three dimensional structures and theirs physiological functions. Moreover, for manufacture cost, it needs considerable cost of machines or solvents for using physical/chemical reagents which are also harmful to the environment or humans.

As a result, it is necessary to provide a method for changing conformation of globular proteins to solve the problems existing in the conventional technologies, as described above.

SUMMARY OF THE INVENTION

A primary object of the present invention is to provide a method for changing conformation of globular proteins, which controls the concentration of the globular proteins and the adsorption time of the globular proteins from the aqueous solution to the air/liquid interface, so that the main conformation of the globular proteins in a protein monolayer can be changed into β-sheet or α-helix. Meanwhile, the protein monolayer having the conformation of β-sheet or α-helix can be vertically deposited and transferred onto a substrate for various applications according to needs. Thus, the present invention can change three-dimensional structures of biological molecules and remain original functions thereof without additionally using any physical/chemical treatment to change the conformation of the globular proteins. Therefore, the present invention can simplify manufacture processes, maintain activities of globular proteins, reduce manufacture cost and lower the harmful impact for the environment.

To achieve the above object, the present invention provides a method for changing conformation of globular proteins, which comprises steps of:

preparing a type of globular proteins;

mixing the globular proteins with water to form a mixture solution;

keeping the mixture solution for a first adsorption time, so that the globular proteins in the mixture solution are absorbed onto an air/liquid interface of the mixture solution to form a protein monolayer, wherein the protein monolayer has a first surface pressure and the conformation of the protein monolayer is mainly β-sheet; and keeping the mixture solution for a second adsorption time, so that the protein monolayer has a second surface pressure and the conformation of the protein monolayer is converted into α-helix, wherein the second surface pressure is higher than the first surface pressure.

In one embodiment of the present invention, the globular proteins are selected from glucose oxidase (GOx), bovine serum albumin (BSA), haemoglobin, immunoglobulin, myoglobin, cytoglobin, flavohaemoglobins, protoglobin, cyanoglobin, ferritin, phospholipase C, concanavalin A, chymotrypsin, insulin, pancreatic trypsin inhibitor, lysozyme, fibrinogen, RNase A, alcohol dehydrogenase, hexokinase or phosphorylase.

In one embodiment of the present invention, the globular proteins are selected from glucose oxidase (GOx) and the concentration of the globular proteins in the mixture solution is between 4.98 mg/kg and 19.92 mg/kg. The first absorption time is 0.5 to 4 hours after starting to keep the mixture solution; and the second absorption time is 8 hours or more after starting to keep the mixture solution. The first surface pressure is between 6 mN/m and 8 mN/m; and the second surface pressure is between 14 mN/m and 16 mN/m. A measured α-helix/β-sheet ratio of the protein monolayer is equal to or smaller than 0.09 at the first absorption time; and the measured α-helix/β-sheet ratio of the protein monolayer is equal to or smaller than 9.095 at the second absorption time.

In one embodiment of the present invention, the globular proteins are selected from bovine serum albumin (BSA), and the concentration of the globular proteins in the mixture solution is between 0.01 mg/L and 0.08 mg/L. The first absorption time is 1.5 to 12 hours after starting to keep the mixture solution; and the second absorption time is 24 hours or more after starting to keep the mixture solution. The first surface pressure is between 2 mN/m and 3 mN/m; and the second surface pressure is between 7 mN/m and 8 mN/m. A measured α-helix/β-sheet ratio of the protein monolayer is equal to or smaller than 2.07 at the first absorption time; and the measured α-helix/β-sheet ratio of the protein monolayer is equal to or smaller than 6.14 at the second absorption time.

In one embodiment of the present invention, the globular proteins are selected from haemoglobin, and the concentration of the globular proteins in the mixture solution is between 0.05 mg/L and 0.2 mg/L. The first absorption time is 1.5 to 12 hours after starting to keep the mixture solution; and the second absorption time is 24 hours or more after starting to keep the mixture solution. The first surface pressure is between 2 mN/m and 3 mN/m; and the second surface pressure is between 7 mN/m and 8 mN/m. A measured α-helix/β-sheet ratio of the protein monolayer is equal to or smaller than 0.21 at the first absorption time; and the measured α-helix/β-sheet ratio of the protein monolayer is equal to or smaller than 8.78 at the second absorption time.

In one embodiment of the present invention, the globular proteins are selected from immunoglobulins, and the concentration of the globular proteins in the mixture solution is between 0.1 mg/L and 0.5 mg/L. The first absorption time is 1.5 to 12 hours after starting to keep the mixture solution; and the second absorption time is 24 hours or more after starting to keep the mixture solution. The first surface pressure is between 2 mN/m and 3 mN/m; and the second surface pressure is between 7 mN/m and 8 mN/m. A measured α-helix/β-sheet ratio of the protein monolayer is equal to or smaller than 0.15 at the first absorption time; and the measured α-helix/β-sheet ratio of the protein monolayer is equal to or smaller than 8.99 at the second absorption time.

In one embodiment of the present invention, the step of keeping the mixture solution for the first adsorption time further comprises: vertically depositing and transferring the protein monolayer of the air/liquid interface onto a first substrate.

In one embodiment of the present invention, the first substrate is selected from a biochip substrate, a sensor substrate or a detection/analysis substrate. For example, the first substrate is selected from a quartz substrate, a platinum substrate, a rigid transparent plastic substrate or a flexible transparent plastic substrate.

In one embodiment of the present invention, the step of keeping the mixture solution for the second adsorption time further comprises: vertically depositing and transferring the protein monolayer of the air/liquid interface onto a second substrate.

In one embodiment of the present invention, the second substrate is selected from a biochip substrate, a sensor substrate or a detection/analysis substrate. For example, the second substrate is selected from a quartz substrate, a platinum substrate, a rigid transparent plastic substrate or a flexible transparent plastic substrate.

Figure 1:
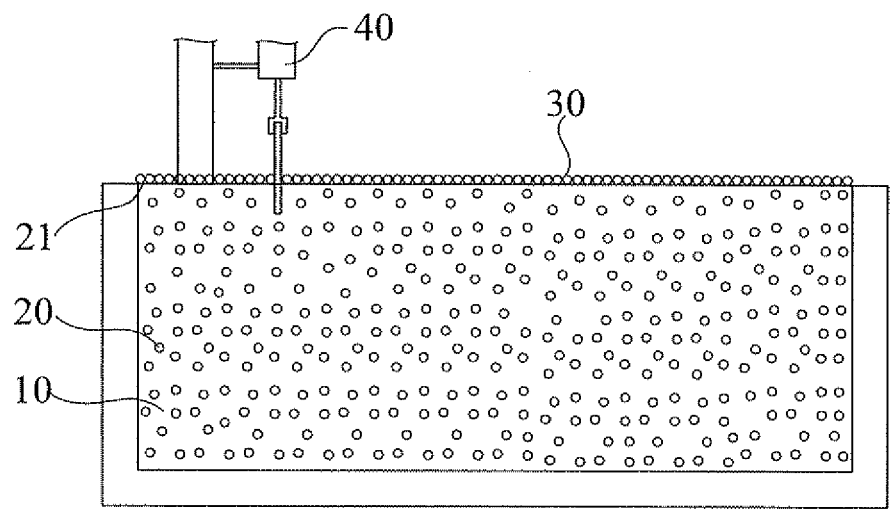
FIG. 1 is a schematic view of measuring the surface pressure of a protein monolayer by a surface-pressure measuring device according to a method for changing conformation of globular proteins of a first embodiment of the present invention.

The numeral labels in abovementioned figures refer to the terms as described below.

"globular protein (label 10 in FIGS. 1 and 3); mixture solution (label 20 in FIGS. 1 and 3); air/liquid interface (label 21 in FIGS. 1 and 3); protein monolayer (label 30 in FIGS. 1 and 3); surface pressure measuring device (label 40 in FIGS. 1 and 3); first substrate (label 50 in FIGS. 3 and 4); second substrate (label 50' in FIG. 4); counter electrode (label 61 in FIG. 4); reference electrode (label 62 in FIG. 4); and glucose solution (label 70 in FIG. 4)".

DETAILED DESCRIPTION OF THE PREFERRED EMBODIMENTS

The structure and the technical means adopted by the present invention to achieve the above and other objects can be best understood by referring to the following detailed description of the preferred embodiments and the accompanying drawings. Furthermore, directional terms described by the present invention, such as upper, lower, front, back, left, right, inner, outer, side, longitudinal/vertical, transverse/horizontal, and etc., are only directions by referring to the accompanying drawings, and thus the used directional terms are used to describe and understand the present invention, but the present invention is not limited thereto.

Referring now to FIG. 1, a method for changing conformation of a globular proteins according to a first embodiment of the present invention is illustrated. As shown, the method comprises steps of: preparing a globular protein (label 10 in FIGS. 1 and 3); mixing the globular protein with water to form a mixture solution (label 20 in FIGS. 1 and 3); allowing the mixture solution to stand for a first adsorption time, so that the globular protein in the mixture solution is adsorbed onto an air/liquid interface (label 21 in FIGS. 1 and 3 of the mixture solution to form a protein monolayer (label 30 in FIGS. 1 and 3), wherein the protein monolayer has a fast surface pressure and the conformation of the protein monolayer is mainly β-sheet; and allowing the mixture solution to stand for a second adsorption time, so that the protein monolayer has a second surface pressure and the conformation of the protein monolayer is converted into α-helix, wherein the second surface pressure is higher than the first surface pressure. The content and principle of all steps of the present invention are described in details with FIG. 1 to FIG. 6 hereinafter.

Figure 3:
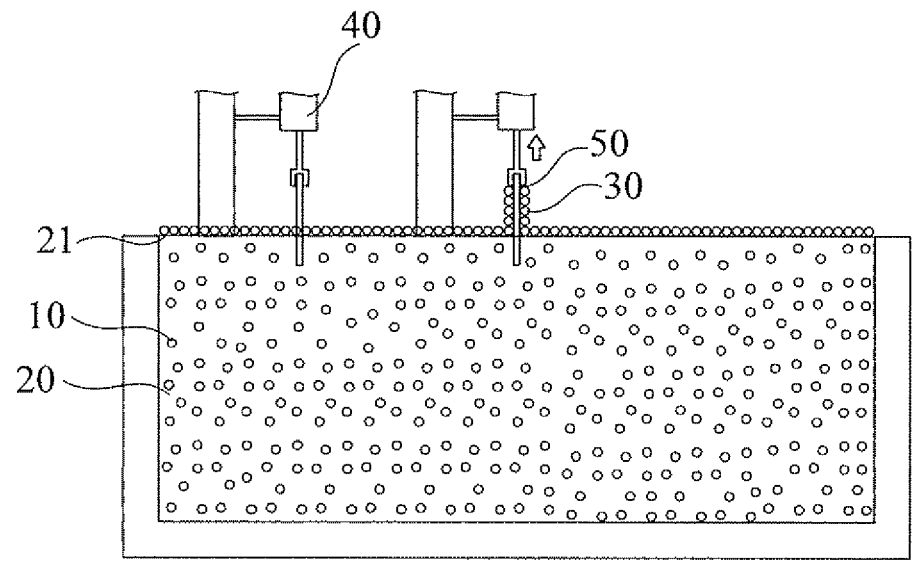
FIG. 3 is a schematic view of the protein monolayer vertically deposited and transferred onto a first substrate according to the method of the first embodiment of the present invention.

First, the method for changing conformation of globular protein according to the first embodiment of the present invention is to provide a globular protein (label 10 in FIGS. 1 and 3). In the present invention, the globular protein is selected from glucose oxidase (GOx), bovine serum albumin (BSA), haemoglobin, immunoglobulin, myoglobin, cytoglobin, flavohaemoglobins, protoglobin, cyanoglobin, ferritin, phospholipase C, concanavalin A, chymotrypsin, insulin, pancreatic trypsin inhibitor, lysozyme, fibrinogen, RNase A, alcohol dehydrogenase, hexokinase and phosphorylase. For examples, in the first embodiment of the present invention, the globular protein is glucose oxidase (GOx).

Next, referring to FIG. 1, the method for changing conformation of globular protein according to the first embodiment of the present invention is to mix the globular protein with water forming a mixture solution (label 20 in FIGS. 1 and 3). In this step, the concentration of the globular protein in the mixture solution is depended on the type of globular protein. For examples, in the first embodiment of the present invention, if the globular protein is glucose oxidase (GOx), the concentration of the globular protein in the mixture solution is between 4.98 mg/L and 19.92 mg/L. For example, the concentration is preferably 9.96 mg/L, but not limited thereto.

Figure 2:
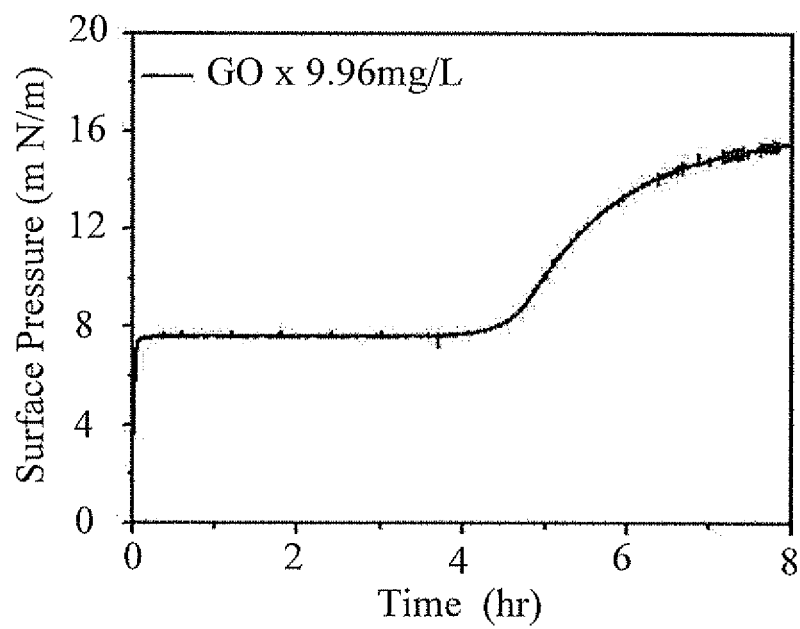
FIG. 2 is a surface pressure/time diagram of the protein monolayer of globular proteins (glucose oxidase, GOx) according to the method of the first embodiment of the present invention.

Then, referring to FIGS. 1 and 2, the method for changing conformation of globular protein according to the first embodiment of the present invention is to allow the mixture solution to stand for a first adsorption time, so that the globular protein in the mixture solution is adsorbed onto the air/liquid interface of the mixture solution to form the protein monolayer 30, wherein the protein monolayer has a first surface pressure and the conformation of the protein monolayer is mainly β-sheet. In the embodiment of the present invention, the mixture solution is filled into a container, and a surface pressure measuring device (label 40 in FIGS. 1 and 3) is used to detect a surface pressure of the air/liquid interface, wherein a liquid surface layer of the mixture solution is defined as the air/liquid interface which is an interface of the mixture solution in contact with to the atmosphere. Furthermore, the container can be a tank of Langmuir Film Balance, but is not limited thereto. For example, it also can be a simple water tank. After allowing the mixture solution to stand for the first adsorption time, the globular protein of the mixture solution gradually adsorbs to the air/liquid interface of the mixture solution to form the protein monolayer.

Simultaneously the present invention uses the surface pressure measuring device to detect the variation of surface pressure of the protein monolayer according to the adsorption time, wherein the surface pressure measuring device is connected to a computer system (not shown) for continually recording the statistic values of the variation of the surface pressure with time, so as to draw a surface pressure/time diagram as shown in FIG. 2.

Referring to FIG. 2, if the globular protein is glucose oxidase (GOx), as described above, the first adsorption time is any time point within 0.5 hour to 4 hours after starting to allow the mixture solution to stand for the first adsorption time, such as the time point of 0.5 hour after starting, as shown in FIG. 2. Within the period of the first adsorption time (i.e. 0.5 hours to 4 hours after starting), the surface pressure of the protein monolayer achieves to a stage of nearly balance, wherein the surface pressure maintains to approach a first surface pressure which is between about 6 mN/m and about 8 mN/m, such as 7.5 mN/m. At this time, the globular protein of the mixture solution is adsorbed to the air/liquid interface of the mixture solution, so as to form the protein monolayer which is mainly β-sheet.

Figure 4:
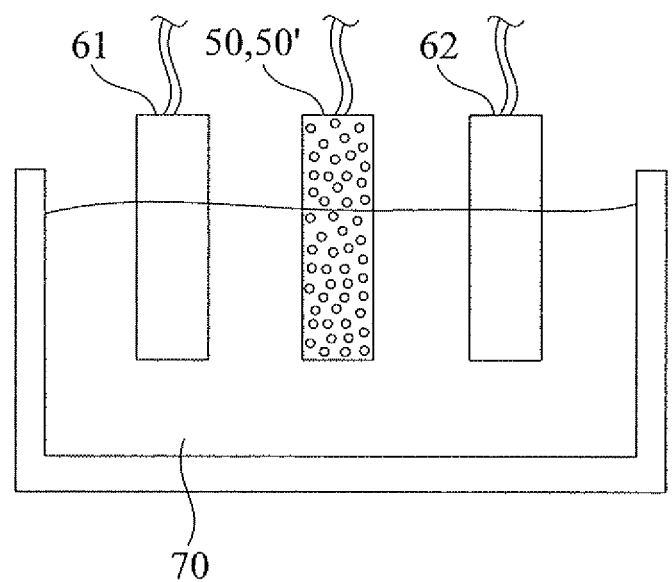
FIG. 4 is a schematic view of chronoamperometry by immersing the first substrate and/or a second substrate in a glucose solution according to the method of the first embodiment of the present invention.

Referring to FIG. 3, in order to detect a measured α-helix/β-sheet ratio of the protein monolayer during the period of the first adsorption time, the method of the present invention comprises a step of vertically depositing and transferring the protein monolayer of the air/liquid interface onto a first substrate (label 50 in FIGS. 3 and 4). In the embodiment of the present invention, the first substrate is a substrate for detecting/analyzing, such as a quartz (glass) plate. The present invention executes the vertical depositions 100 times to transfer 100 layers of the protein monolayer onto the first substrate (the transfer rates are at 1 and 150 mm/min in the downward/upward directions, respectively). And then, the secondary structure of the protein monolayer is examined by circular dichroism (CD). Results are listed in Table 1, as follows:

TABLE 1 conformation comparison of glucose oxidase (GOx) at different adsorption time.

| Absorption time (hr) | α-helix | β-sheet | α/β |
|---|---|---|---|
| 0.5 | 4.23 | 46.99 | 0.090 |
| 8 | 54.84 | 6.03 | 9.095 |

Referring to Table 1, the measured α-helix/β-sheet ratio of the protein monolayer is equal to (or smaller than) 0.09 at the first adsorption time and the conformation of the protein monolayer is mainly β-sheet. Moreover, the protein monolayer is deposited and transferred onto the first substrate, wherein the numbers of deposited layers is according to needs of application. Beside of a substrate for detecting/analyzing, the first substrate also can be a biochip substrate or a sensor substrate; the material of the first substrate is not limited to quartz substrate, and also can be a platinum substrate, a rigid transparent plastic substrate or a flexible transparent plastic substrate, but not limited thereto.

Finally, refer to FIGS. 1, 2, 3, and Table 1, the method for changing conformation of a globular proteins according to the first embodiment of the present invention is to allow the mixture solution to stand for a second adsorption time, so that the globular protein in the mixture solution are adsorbed onto the air/liquid interface of the mixture solution to forming the protein monolayer, wherein the protein monolayer has a second surface pressure and the conformation of the protein monolayer is mainly α-helix, wherein the second surface pressure is higher than the first surface pressure. In the embodiment of the present invention, the second adsorption time is any time point from 8 to more hours after starting to allows the mixture solution to stand for the first adsorption time, such as the time point of 8 hours after starting, as shown in FIG. 2. Within the period from the first adsorption time to the second adsorption time (i.e. from 4.5 hours to 7.5 hours after starting), the surface pressure of the protein monolayer is changed and increased by time. Next, within the period of the second adsorption time (8 hours or more after starting), the surface pressure of the protein monolayer achieves to another stage of nearly balance, and the surface pressure maintains around a second surface pressure which is between about 14 mN/m and about 16 mN/m, such as around 15.5 mN/m. At the second adsorption time, the conformation of the protein monolayer is mainly α-helix, and the measured α-helix/β-sheet ratio of the protein monolayer is equal to (or larger than) 9.095, i.e. the conformation is mainly α-helix.

In the present and forward steps, the globular protein is large complex molecules constructed by different types of amino acids, so the globular protein shows asymmetric distributions of hydrophilic and hydrophobic properties, wherein the globular protein can adsorbe to the air/liquid interface to form the protein monolayer spontaneously according to the hydrophilic and hydrophobic properties thereof. And, the molecular conformation of the globular protein can be converted to provide different molecular conformations according to hydrophilic and hydrophobic phases of the air/liquid interface, and these different molecular conformations of the globular protein can be applied to various applications. For examples, in the present step, similar to the forward step, the protein monolayer can be vertically deposited and transferred onto a second substrate (label 50' in FIG. 4), wherein the numbers of deposited layers are according to needs of application. The second substrate is similarly selected from a biochip substrate, a sensor substrate and a substrate for detecting/analyzing; and the material of the second substrate can be selected from a quartz substrate, a platinum substrate, a rigid transparent plastic substrate and a flexible transparent plastic substrate, but not limited thereto.

Figure 5:
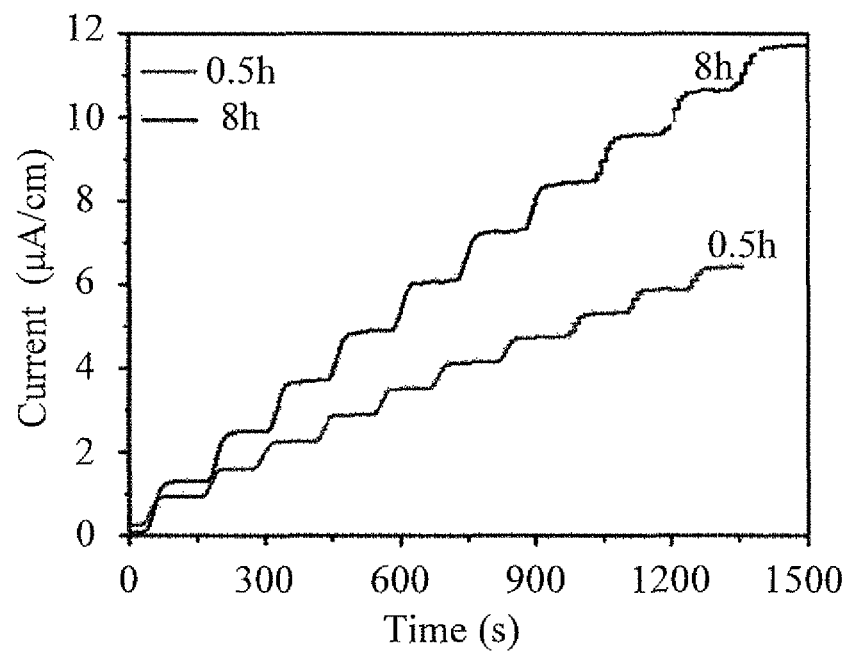
FIG. 5 is a current/time diagram of chronoamperometry according to FIG. 4 of the present invention.

Moreover, refer to FIGS. 4 and 5, the first embodiment of the present invention provides the first substrate vertically deposited with the protein monolayer at the first adsorption time (the first adsorption time of 0.5 hours, the measured α-helix/β-sheet ratio is equal to or smaller than 0.09); or the second substrate vertically deposited with the protein monolayer at the second adsorption time (the second adsorption time is 8 hours, the measured α-helix/β-sheet ratio is equal to or larger than 9.095), wherein the first substrate and the second substrate can be used as a working electrode. Simultaneously, a platinum plate is used as a counter electrode (label 61 in FIG. 4) and an Ag/AgCl plate is used as a reference electrode (label 62 in FIG. 4). Then, these three electrodes are immersed into a glucose solution (label 70 in FIG. 4. The globular protein (i.e. GOx) of the protein monolayer on the first substrate (or the second substrate) catalyzes and converts the glucose solution (0.5 mM) into gluconic acid and $H_2O_2$, wherein this reaction is detected by chronoamperometry, and a constant potential (0.6V to Ag/AgCl electrode) is applied to the glucose solution to detect current variation of $H_2O_2$ generation, then the current/time diagram is shown in FIG. 5. As shown in the current variation of FIG. 5, regardless of the conformations (β-sheet or α-helix), the globular protein on the surface of the first substrate (adsorption time is 0.5 hours) or the second substrate (adsorption time is 8 hours), the conformations can maintain original physiological functions of enzyme proteins.

Figure 6:
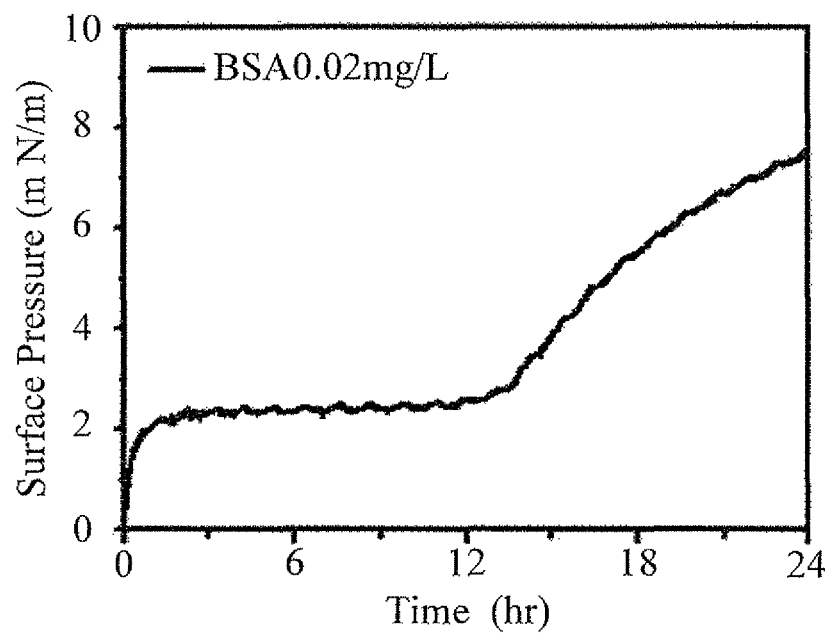
FIG. 6 is a surface pressure/time diagram of a protein monolayer of globular proteins (bovine serum albumin, BSA) according to a method for changing conformation of globular proteins of a second embodiment of the present invention.

Refer to FIG. 6, the second embodiment of the present invention has the same method for changing conformation of globular protein as described above, but the globular protein of the second embodiment is bovine serum albumin (BSA), wherein the concentration of the globular protein in the mixture solution is between 0.01 mg/L and 0.08 mg/L, such as 0.02 mg/L. The first adsorption time is 1.5 hours to 12 hours after starting to allow the mixture solution to stand for the first adsorption time, such as 1.5 hours. The second adsorption time is 24 hours or more after starting to allow the mixture solution to stand for the first adsorption time, such as 24 hours. The first surface pressure is between 2 mN/m and 3 mN/m, such as about 2.3 mN/m; and the second surface pressure is between 7 mN/m and 8 mN/m, such as about 7.3 mN/m. The measured α-helix/β-sheet ratio of the protein monolayer is equal to or smaller than 2.07 at the first adsorption time, and the conformation is mainly β-sheet; and the measured α-helix/β-sheet ratio of the protein monolayer is equal to or larger than 6.14 at the second adsorption time, and the conformation is mainly α-helix.

Similarly, the third embodiment of the present invention has the same method for changing conformation of a globular protein as described above, but the globular protein of the third embodiment is haemoglobin which has the concentration of the globular protein in the mixture solution is between 0.05 mg/L and 0.2 mg/L, such as 0.1 mg/L. The first adsorption time is 1.5 hours to 12 hours after starting to allow the mixture solution to stand for the first adsorption time, such as 1.5 hours. The second adsorption time is 24 hours or more after starting to allow the mixture solution to stand for the first adsorption time, such as 24 hours. The first surface pressure is between 2 mN/m and 3 mN/m, such as about 2.3 mN/m; and the second surface pressure is between 7 mN/m and 8 mN/m, such as about 7.3 mN/m. The measured α-helix/β-sheet ratio of the protein monolayer 30 is equal to or smaller than 0.21 at the first adsorption time, and the conformation is mainly β-sheet; and the measured α-helix/β-sheet ratio of the protein monolayer is equal to or larger than 8.78 at the second adsorption time, and the conformation is mainly α-helix.

Furthermore, the fourth embodiment of the present invention has the same method for changing conformation of a globular protein as described above, but the globular protein of the fourth embodiment is immunoglobulins, wherein the concentration of the globular protein in the mixture solution is between 0.1 mg/L and 0.5 mg/L, such as 0.25 mg/L. The first adsorption time is 1.5 hours to 12 hours after starting to allow the mixture solution to stand for the first adsorption time, such as 1.5 hours. The second adsorption time is 24 hours or more after starting to allow the mixture solution to stand for the first adsorption time, such as 24 hours. The first surface pressure is between 2 mN/m and 3 mN/m, such as about 2.3 mN/m; and the second surface pressure is between 7 mN/m and 8 mN/m, such as about 7.3 mN/m. The measured α-helix/β-sheet ratio of the protein monolayer is equal to or smaller than 0.15 at the first adsorption time, and the conformation is mainly β-sheet; and the measured α-helix/β-sheet ratio of the protein monolayer is equal to or larger than 8.99 at the second adsorption time, and the conformation is mainly α-helix.

As described above, in comparison with the conventional method of changing protein conformation which is changed by physical or chemical treatment, easily loss theirs physiological functions and thus get the disadvantages of increasing treatment cost and rising dangers to the environment or humans, the present invention as shown in FIGS. 1 to 6 controls the concentration of the globular protein and the adsorption time for adsorbing the globular protein from the mixture solution to the air/liquid interface, so as to change the conformation of the protein monolayer of the globular protein until the conformation is mainly β-sheet or α-helix. Moreover, the first substrate- and the second substrate can be used to deposit vertically and transfer β-sheet or α-helix conformations of the protein monolayer. Therefore, the described techniques of the present invention can change the three dimensional structure of biomolecules for being applied to various applications, and remain original functions thereof without additionally using any physical or chemical treatment to change the conformation of the globular protein. Therefore, the present invention is advantageous to simplify manufacture processes, maintain activities of a globular protein, reduce manufacture cost and lower the harmful impact for the environment.

The present invention has been described with a preferred embodiment thereof and it is understood that many changes and modifications to the described embodiment can be carried out without departing from the scope and the spirit of the invention that is intended to be limited only by the appended claims.

What is claimed is:
1. A method for changing conformation of globular proteins,
comprising steps of:
preparing a globular protein;
mixing the globular protein with water to form a mixture solution;

allowing the mixture solution to stand for a first adsorption time without using a binding layer, so that the globular protein in the mixture solution is adsorbed onto an air/liquid interface of the mixture solution to form a protein monolayer, wherein the protein monolayer has a first surface pressure and the conformation of the protein monolayer is mainly β-sheet; and allowing the mixture solution to stand for a second adsorption time, so that the protein monolayer has a second surface pressure and the conformation of the protein monolayer is converted into α-helix;

wherein the second surface pressure is higher than the first surface pressured the globular protein is glucose oxidase; and the concentration of the globular protein of the mixture solution is between 4.98 mg/L and 19.92 mg/L.

2. The method according to claim 1, wherein the first adsorption time is 0.5 to 4 hours and the second adsorption time is 8 or more hours.

3. The method according to claim 1, wherein the first surface pressure is between 6 mN/m and 8 mN/m; and the second surface pressure is between 14 mN/m and 16 mN/m.

4. The method according to claim 1, wherein a measured α-helix/β-sheet ratio of the protein monolayer is equal to or smaller than 0.09 at the first adsorption time; and the measured α-helix/β-sheet ratio of the protein monolayer is equal to or larger than 9.095 at the second adsorption time.

5. The method according to claim 1, wherein the first surface pressure is between 2 mN/m and 3 mN/m; and the second surface pressure is between 7 mN/m and 8 mN/m.

6. The method according to claim 1, wherein the method further comprises vertically depositing and transferring the protein monolayer of the air/liquid interface onto a first substrate after the first adsorption time.

7. The method according to claim 6, wherein the first substrate is a biochip substrate a sensor substrate.

8. The method according to claim 1, wherein the method further comprises vertically depositing and transferring the protein monolayer of the air/liquid interface onto a substrate after the second adsorption time.

9. The method according to claim 8, wherein the substrate is a biochip substrate or a sensor substrate.

* * * * *

UNITED STATES PATENT AND TRADEMARK OFFICE
CERTIFICATE OF CORRECTION

Page 1 of 1

PATENT NO. : 9,120,844 B2
APPLICATION NO. : 13/479294
DATED : September 1, 2015
INVENTOR(S) : Yuh-lang Lee et al.

It is certified that error appears in the above-identified patent and that said Letters Patent is hereby corrected as shown below:

In the claims:

Column 10, Claim 7 line 14 should be corrected as follows:
Change
-- substrate a sensor --
to
"substrate or a sensor"

Signed and Sealed this
Ninth Day of February, 2016

Michelle K. Lee
*Director of the United States Patent and Trademark Office*